United States Patent
Zinovik et al.

(10) Patent No.: US 10,912,334 B2
(45) Date of Patent: *Feb. 9, 2021

(54) FLAVOURED NICOTINE POWDER INHALER

(71) Applicant: PHILIP MORRIS PRODUCTS S.A., Neuchatel (CH)

(72) Inventors: Ihar Nikolaevich Zinovik, Peseux (CH); Gerard Zuber, Froideville (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/124,592

(22) PCT Filed: Apr. 23, 2015

(86) PCT No.: PCT/IB2015/001283
§ 371 (c)(1),
(2) Date: Sep. 8, 2016

(87) PCT Pub. No.: WO2015/166350
PCT Pub. Date: Nov. 5, 2015

(65) Prior Publication Data
US 2017/0035108 A1    Feb. 9, 2017

Related U.S. Application Data

(60) Provisional application No. 61/984,968, filed on Apr. 28, 2014.

(30) Foreign Application Priority Data

Apr. 28, 2014 (EP) ................................ 14166210

(51) Int. Cl.
A24F 47/00     (2020.01)
A61M 15/00     (2006.01)
(Continued)

(52) U.S. Cl.
CPC ............ *A24F 47/002* (2013.01); *A24B 15/16* (2013.01); *A61K 9/0075* (2013.01);
(Continued)

(58) Field of Classification Search
CPC ............. A24F 47/002; A61M 15/0036; A61M 15/003; A61M 15/0008
See application file for complete search history.

(56) References Cited

U.S. PATENT DOCUMENTS 4,597,961 A   7/1986  Etscorn
4,655,229 A   4/1987  Sensabaugh, Jr. et al.
(Continued)

FOREIGN PATENT DOCUMENTS

CN    1292714 A    4/2001
CN    1079267      2/2002
(Continued)

OTHER PUBLICATIONS

International Preliminary Report on Patentability for PCT/IB2015/001283, issued by the International Bureau of WIPO dated Nov. 10, 2016, 6 pgs.
(Continued)

*Primary Examiner* — Alex B Efta
(74) *Attorney, Agent, or Firm* — Mueting Raasch Group

(57) ABSTRACT

This disclosure relates to flavoured nicotine powder inhalers where the nicotine powder is delivered at air flow rates that mimic a smoking regime.

21 Claims, 6 Drawing Sheets

Figure 1:
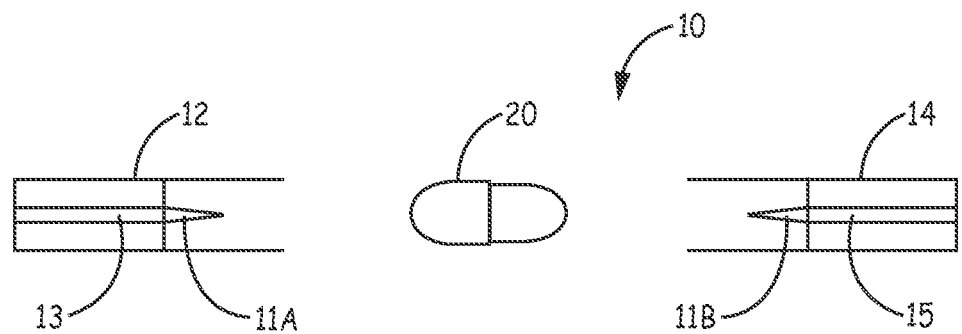

(51) Int. Cl.

| | |
|---|---|
| *A61M 15/06* | (2006.01) |
| *A24B 15/16* | (2020.01) |
| *A61K 9/00* | (2006.01) |
| *A61K 31/465* | (2006.01) |

(52) U.S. Cl.

CPC ......... *A61K 31/465* (2013.01); *A61M 15/003* (2014.02); *A61M 15/0021* (2014.02); *A61M 15/0028* (2013.01); *A61M 15/0036* (2014.02); *A61M 2202/064* (2013.01); *A61M 2206/16* (2013.01)

(56) References Cited

U.S. PATENT DOCUMENTS

| | | | |
|---|---|---|---|
| 4,735,217 A | 4/1988 | Gerth et al. | |
| 5,441,060 A | 8/1995 | Rose et al. | |
| 5,687,710 A * | 11/1997 | Ambrosio | A61M 15/0065 128/203.15 |
| 5,746,227 A | 5/1998 | Rose et al. | |
| 6,098,632 A * | 8/2000 | Turner | A24F 47/002 131/270 |
| 7,089,934 B2 * | 8/2006 | Staniforth | A61J 7/0038 128/203.12 |
| 8,256,433 B2 | 9/2012 | Gonda | |
| 8,561,609 B2 | 10/2013 | Donovon et al. | |
| 2001/0026788 A1 | 10/2001 | Piskorz | |
| 2002/0092521 A1 | 7/2002 | Sullivan et al. | |
| 2002/0092524 A1 | 7/2002 | Lockhart et al. | |
| 2003/0183228 A1 | 10/2003 | Clark et al. | |
| 2004/0079363 A1 | 4/2004 | Casper et al. | |
| 2005/0022812 A1 * | 2/2005 | Hrkach | A61M 15/0021 128/203.15 |
| 2006/0147389 A1 * | 7/2006 | Staniforth | A61K 9/0073 424/46 |
| 2007/0062548 A1 | 3/2007 | Horstmann et al. | |
| 2007/0175476 A1 | 8/2007 | Lipowicz | |
| 2008/0241255 A1 | 10/2008 | Rose et al. | |
| 2011/0220106 A1 * | 9/2011 | Ganem | A61M 15/0028 128/203.21 |
| 2011/0297166 A1 | 12/2011 | Takeuchi et al. | |
| 2012/0145150 A1 | 6/2012 | Donovan et al. | |
| 2013/0160780 A1 | 6/2013 | Matsumoto et al. | |
| 2013/0180524 A1 | 7/2013 | Shahaf et al. | |
| 2013/0333699 A1 * | 12/2013 | Chen | A61M 15/0028 128/203.15 |
| 2014/0088044 A1 | 3/2014 | Rigas et al. | |

FOREIGN PATENT DOCUMENTS

| | | | |
|---|---|---|---|
| CN | 2609565 Y | 4/2004 | |
| CN | 1668355 A | 9/2005 | |
| CN | 2742785 Y | 11/2005 | |
| CN | 1805731 A | 7/2006 | |
| CN | 1889861 A | 1/2007 | |
| CN | 102355914 A | 2/2012 | |
| CN | 102395398 A | 3/2012 | |
| CN | 101351238 B | 4/2012 | |
| CN | 103068266 A | 4/2013 | |
| CN | 103566444 A | 2/2014 | |
| EP | 2082764 A1 * | 7/2009 | ........ A61M 15/0045 |
| EP | 2 399 637 A1 | 12/2011 | |
| GB | 2 461 008 A | 12/2009 | |
| GB | 2 497 616 A | 6/2013 | |
| JP | S6012581 A | 10/1985 | |
| JP | 2002522173 A | 7/2002 | |
| JP | 2009521970 A | 6/2009 | |
| WO | WO 91/01656 A1 | 2/1991 | |
| WO | WO 91/18636 A1 | 12/1991 | |
| WO | WO 97/12639 A1 | 4/1997 | |
| WO | WO-9712639 A1 * | 4/1997 | ........... A24F 47/002 |
| WO | WO 00/09188 A1 | 2/2000 | |
| WO | WO 03/090715 A2 | 11/2003 | |
| WO | WO 03/097142 A1 | 11/2003 | |
| WO | WO 2005/049449 A1 | 6/2005 | |
| WO | WO 2007/091126 A2 | 8/2007 | |
| WO | WO 2010/095659 A1 | 8/2010 | |
| WO | WO 2010/130982 A2 | 11/2010 | |
| WO | WO 2013/128447 A1 | 9/2013 | |

OTHER PUBLICATIONS

International Search Report and Written Opinion for PCT/IB2015/001283, issued by the European Patent Office as the International Search Authority, dated Nov. 18, 2015; 9 pgs.

Extended European Search Report for EP 14166210.6, issued by the European Patent Office, dated Nov. 10, 2014.

First Office Action from the Chinese Patent Office for CN Application No. 201580019508.9; dated Jan. 3, 2019, including English Translation: 20 pgs.

Japanese Office Action, including English Translation, Issued by the Japanese Patent Office dated Feb. 21, 2019 for JP 2016-565032, 11 pgs.

Chinese Office Action, including English Translation, Issued by the Chinese Patent Office dated Jul. 16, 2019 for CN Application No. 201580019508.9, 18 pgs.

Chinese Rejection Decision for CN Application No. 201580019508.9, issued by the China National Intellectual Property Administration dated Nov. 4, 2019; 18 pgs. Including English Translation.

Japanese Decision on Rejection issued by the Japanese Patent Office dated Sep. 26, 2019 for JP Application No. 2016-565032; 10 pgs. Including English Translation.

Taiwan Office Action issued by the Taiwanese Patent Office for TW 104113147, dated Mar. 18, 2020; 15 pgs.

* cited by examiner

FLAVOURED NICOTINE POWDER INHALER

This application is the § 371 U.S. National Stage of International Application No. PCT/IB2015/001283, filed 23 Apr. 2015, which claims the benefit of U.S. Provisional Application No. 61/984,968, filed 28 Apr. 2014 and EP Application No. 14166210.6, filed 28 Apr. 2014, each of which are incorporated by reference herein.

This disclosure relates to flavoured nicotine powder inhalers, where the flavoured nicotine powder is delivered at low air flow rates.

Dry powder inhalers (DPI) are known and are used to treat respiratory diseases by delivering a dry powder comprising a pharmaceutical, in aerosol form through inhalation to the patients' airways. For delivery deep into the lungs, particles in the range of 1 to 5 micrometers are required. In pharmaceutical dry powders, the active pharmaceutical ingredient (API) is agglomerated on the surface of larger carrier particles, e.g. lactose, and DPI's therefore operate complex mechanisms to ensure such agglomerates disperse, break up or disaggregate before the API can be inhaled deep into the lungs. Pharmaceutical dry powders containing lactose as a carrier are typically in the range of 20 to 100 micrometers. Existing DPI's for example first "grind" or de-agglomerate the dry powder or impact the larger particles of the dry powder to result in the aforementioned particle size range.

DPI's rely on the force of the patients' inhalation to entrain the powder from the device to subsequently break-up the powder into particles that are small enough to enter the lungs. Sufficiently high inhalation rates are required to ascertain correct dosing and complete disaggregation of the powder. Typically a large amount of API remains attached on the surface of the carrier and is deposited in the upper airways due to incomplete de-aggregation of the powder. Inhalation rates of existing DPI's are usually in the range of 40-120 liters/min (L/min). Existing DPI's are therefore only suitable for delivering dry powders to users in a manner that is different from the inhalation rate associated with smoking articles.

It would be desirable to provide a flavoured nicotine powder inhaler that can deliver flavoured nicotine powder to a user at inhalation or air flow rates that are within conventional smoking regime inhalation or air flow rates. It would be desirable to provide a flavoured nicotine powder inhaler that is a similar size and configuration as a conventional cigarette. It would be desirable to provide a flavoured nicotine powder inhaler that can provide a metered dose of flavoured nicotine and an optional simultaneous delivery of a second active ingredient.

Flavoured nicotine powder inhalers of the invention described herein can be utilized to deliver flavoured nicotine to a user at inhalation or air flow rates that are close to or within conventional smoking regime inhalation or air flow rates. The flavoured nicotine powder inhalers can provide a predictable and metered dose of flavoured nicotine or other optional active ingredients. Flavoured nicotine powder inhalers of the invention described herein have a similar size and configuration as a conventional cigarette and have a simple configuration.

As described herein, a flavoured nicotine powder inhaler includes a body extending between a mouthpiece and a distal end portion and an airflow channel extends along the body of the inhaler. A nicotine powder receptacle along the airflow channel holds a dose of nicotine powder. A flavour delivery element is in fluid communication with the airflow channel. The dose of nicotine powder can be inhaled into lungs of a user at an inhalation rate of less than about 5 L/min or preferable less than about 2 L/min. Preferably the dose of nicotine powder is a nicotine salt contained in a capsule that can be pierced by the inhaler.

Various aspects of the flavoured nicotine powder inhalers described herein may have one or more advantages relative to standard dry powder inhalers. For example, the flavoured nicotine powder inhalers deliver the dry powder nicotine and the flavour particles at inhalation or air flow rates that are within conventional smoking regime inhalation or air flow rates and inhalation manner. This allows users with even compromised or impaired breathing conditions to successfully deliver the dry powder nicotine and flavourant. The flavoured nicotine powder inhalers described herein have a simplified configuration that allows the user to predetermine the metered dose of dry powder nicotine and flavourant. The dry powder nicotine can be in series or in parallel flow relation with the flavour delivery element. The flavourant can be a dry powder or a liquid flavourant. Additional advantages of one or more aspects flavour delivery system described herein will be evident to those of skill in the art upon reading and understanding the present disclosure.

The term "nicotine" refers to nicotine and nicotine derivatives such as nicotine salts.

The term "flavourant" or "flavour" refers to organoleptic compounds, compositions, or materials that alter the taste or aroma characteristics of nicotine during consumption or inhalation thereof.

The present disclosure provides flavoured nicotine powder inhalers for inhaling dry powder nicotine and flavourant. The flavoured nicotine powder inhalers include a body extending between a mouthpiece portion and a distal end portion. An airflow channel extends between the mouthpiece portion and a distal end portion and a nicotine powder receptacle. The nicotine powder receptacle is disposed along the airflow channel and is configured to receive a dose of nicotine powder. A flavour delivery element is in fluid communication with the airflow channel. The dose of nicotine powder can be inhaled into lungs of a user at an inhalation rate of less than about 5 L/min or less than about 2 L/min which mimics the inhalation flow rate utilized for a conventional smoking regime. The flavourant is delivered to the mouth of the user simultaneously as the nicotine particles are inhaled. The flavoured nicotine powder inhalers described herein are "passive" devices that utilize only the inhalation air flow created by the lungs of a user to create air flow though the body of the flavoured nicotine powder inhaler.

The airflow path or airflow channel through the body of the inhaler is a simple path or channel. In many embodiments the airflow path or airflow channel through the body of the inhaler is parallel to a longitudinal axis of the inhaler and is linearly extending along an entire length of the inhaler body. In some embodiments the inhaler includes two or three co-extensive airflow channels. One, two or all three of the airflow channels can include a capsule receptacle. In some embodiments the one or more airflow paths or airflow channels includes a swirl generator element that is configured to induce a rotational movement of the airflow moving through the body of the inhaler. The swirl generator element can discharge into an outlet channel that can be a larger volume than the one or more individual airflow paths or airflow channels.

The nicotine powder receptacle and the flavour delivery element are configured and arranged to provide the nicotine powder and the flavourant simultaneously. In some embodiments the flavourant is a dry powder mixed with the nicotine powder in a capsule, for example. In other embodiments the flavourant is separated from the nicotine powder before inhalation or mixing within the airflow channels of the inhaler. In some of these embodiments the flavourant and the nicotine powder are in serial flow arrangement and disposed within a single flow channel and the flavourant or flavour delivery element is either upstream or downstream of the nicotine powder or nicotine powder receptacle. In other embodiments the flavourant and the nicotine powder are in parallel flow arrangement and disposed within a pair of flow channels where the flavourant and the nicotine powder combine to form a mixture downstream of both the nicotine powder receptacle and the flavour delivery element.

The nicotine powder receptacle can receive a capsule of nicotine powder. The capsule can contain a predetermined amount or dose of nicotine powder and optional flavourant. In many embodiments the capsule can contain enough nicotine powder to provide at least 2 inhalations or "puffs" of nicotine powder, or at least about 5 inhalations or "puffs" of nicotine powder, or at least about 10 inhalations or "puffs" of nicotine powder. In many embodiments the capsule can contain enough nicotine powder to provide from about 5 to 50 inhalations or "puffs" of nicotine powder, or from about 10 to 30 inhalations or "puffs" of nicotine powder. Each inhalation or "puff" of nicotine powder can deliver from about 0.5 mg to about 3 mg of nicotine powder to the lungs of the user or from about 1 mg to about 2 mg of nicotine powder to the lungs of the user or about 1 mg of nicotine powder to the lungs of the user.

In many embodiments the capsule holds or contains at least about 5 mg of nicotine powder or at least about 10 mg of nicotine powder. In many embodiments the capsule holds or contains less than about 30 mg of nicotine powder or less than about 25 mg of nicotine powder, or less than 20 mg of nicotine powder. In many embodiments the capsule holds or contains from about 5 mg to about 30 mg of nicotine powder or from about 10 mg to about 20 mg of nicotine powder.

In embodiments that include the flavourant blended or combined with the nicotine powder within the capsule, the flavourant is present in an amount that provides the desired flavour to each inhalation or "puff" delivered to the user.

The capsule can be formed of an airtight material that can be pierced or punctured by the inhaler. The capsule can formed of a metallic or polymeric material that serves to keep contaminates out of the capsule but can be pierced or punctured by the inhaler during use.

The inhaler can include a piercing element or pair of opposing piercing elements that are configured to pierce the capsule of nicotine powder. The piercing element or pair of opposing piercing elements fluidly connect the airflow channel with the dose of nicotine powder. The piercing element or pair of opposing piercing elements can engage with the capsule of nicotine powder upon loading the capsule of nicotine powder into the nicotine powder receptacle or upon demand by an actuator on the body of the inhaler.

In many embodiments the nicotine powder is a pharmaceutically acceptable nicotine salt or nicotine salt hydrate. Useful nicotine salts or nicotine salt hydrates include nicotine bitartrate, nicotine salicylate, nicotine fumarate, nicotine mono-pyruvate, nicotine glutamate or nicotine hydrochloride, for example. The compound combining with nicotine to form the salt or salt hydrate can be chosen based on its pharmacological effect. For example: nicotine salicylate can be administered for fever relief, as an anti-inflammatory or painkiller; nicotine fumarate can be administered to treat multiple sclerosis; and nicotine mono-pyruvate can be administered for treating chronic obstructive pulmonary disease (COPD) or for weight loss.

The nicotine powder can have any useful size distribution for inhalation delivery into the lungs of a user. In many embodiments at least about 90 wt % of the nicotine powder has a particle size of about 10 micrometers or less, preferably about 7 micrometers or less. The nicotine powder preferably has a mean average diameter size range from about 0.1 to about 10 micrometers, more preferably from about 1 to about 7 micrometers, even more preferably from about 2 to 6 about micrometers.

Conventional formulations for dry powder inhalation typically contain carrier particles that serve to increase the fluidization of the active particles since the active particles are typically too small to be influenced by the airflow though the inhaler. The carrier particles thus were utilized to improve the dose uniformity by acting as a diluent or bulking agent in a formulation. However, the nicotine powder described herein can be carrier-free. Being carrier-free allows the nicotine powder and to be inhaled and delivered to the user's lungs at inhalation or airflow rates that are similar to typical smoking regime inhalation or airflow rates. In addition, since the nicotine powder is carrier-free, the airflow path of the inhaler can have simple geometry or a simple configuration.

The nicotine powder described herein can be a surface modified nicotine salt where the nicotine salt particle is a coated particle. One preferred coating material is L-leucine. These carrier-free nicotine powders are described and are available from Teicos Pharma Inc., Espoo, Finland. One particularly useful nicotine powder is an L-leucine coated nicotine bitartrate.

Flavourants or flavours can be provided as liquid or solid flavours (at room temperature of about 22 degrees centigrade and one atmosphere pressure) and can include flavour formulations, flavour-containing materials and flavour precursors. The flavourant may include one or more natural flavourants, one or more synthetic flavourants, or a combination of natural and synthetic flavourants.

Flavourants or flavours refer to a variety of flavour materials of natural or synthetic origin. They include single compounds and mixtures. Preferably the flavour or flavourant has flavour properties that enhance the experience of the nicotine powder inhaler to, for example, provide an experience similar to that resulting from smoking a combustible smoking article. For example, the flavour or flavourant can enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours and aromas include, but are not limited to, any natural or synthetic flavour or aroma, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours and aromas may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, for example, in Perfume and Flavour Chemicals, 1969, by S. Arctander, Montclair N.J. (USA); Fenaroli's Handbook of Flavour Ingredients, CRC Press or Synthetic Food Adjuncts by M. B. Jacobs, van Nostrand Co., Inc. They are well-known to the person skilled in the art of flavouring, i.e. of imparting an odor or taste to a product.

In some embodiments, the flavourant is a high potency flavourant, and is typically used at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furanol. Other flavourants can only be sensed by humans at higher concentration levels. These flavourants, which are referred to herein as the low potency flavourants, are typically used at levels that results in orders of magnitude higher amounts of flavourant released into the inhalation air. Suitable low potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The flavour delivery element can be in the form of a capsule containing the flavourant. The capsule can be ruptured by mechanical force such as being squeezed or crushed by a use's fingers or other mechanical means activated by the user. The flavourant within the flavour capsule is preferably a liquid flavourant. The flavour capsule can be disposed upstream of the nicotine powder receptacle, but it is preferably downstream of the nicotine powder receptacle. The flavour capsule can be disposed in a filter element.

The flavour delivery element can be a thread element impregnated by flavourant. Preferably the flavourant in these embodiments is menthol. The thread can be disposed in a filter element that is preferably upstream of the nicotine powder receptacle.

The filter element containing the flavour delivery element can be formed of filtering material such as conventional cellulose acetate filtering material. The filtering material can be a plug of filtering material wrapped in paper or plug wrap. The filtering material can be upstream or downstream of the flavour delivery element, preferably the filtering material is disposed both upstream or downstream of the flavour delivery element. In some embodiments the flavour delivery element extends through the filtering material.

A second active agent or ingredient can be delivered along with the flavoured nicotine powder. The second active agent or ingredient can be mixed with the nicotine in the capsule or separate from the nicotine in its own capsule. The second active agent or ingredient can be fluidized with the flavoured nicotine powder and inhaled by a user.

This second active agent or ingredient can be any active pharmaceutical material. In many embodiments the second active agent or ingredient can be combined with the nicotine powder and flavourant described herein by blending the materials during inhalation. The nicotine powder, flavourant and the second active agent or ingredient can be blended in the same capsule or provided in series in a single air flow channel in the DPI or provided in parallel in separate flow channels of the DPI. The second active agent or ingredient can have a similar mean average diameter size range as the nicotine powder described above.

The flavoured nicotine powder inhaler is less complex and has a simplified powder storage and airflow path as compared to existing DPIs, and does not need a carrier ingredient, such as lactose, as described above. Therefore the complex mechanisms to dissociate/disaggregate a pharmaceutical dry powder is not required in the described flavoured nicotine inhaler and therefore the described nicotine inhaler operates under low airflow. The inhaler does not require the typical high inhalation rates of conventional DPIs to deliver the dry nicotine powders described above deep into the lungs.

The flavoured nicotine inhaler according to this invention operates using a flow rate of less than about 5 L/min or less than about 3 L/min or less than about 2 L/min or about 1.6 L/min. In many embodiments the flow rate is in a range from about 1 L/min to about 3 L/min or from about 1.5 L/min to about 2.5 L/min. In preferred embodiments the inhalation rate or flow rate is similar to that of Health Canada smoking regime, that is about 1.6 L/min. In contrast, a conventional DPI operates at a flow rate of about 40-120 L/min and often requires an energy source or propellant to promote air flow to achieve this air flow rate.

The flavoured nicotine inhaler described herein can be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer can determine the amount of nicotine to be inhaled. During the second step, the consumer can determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIGS. 1-11 are schematic diagrams of illustrative flavoured nicotine powder inhalers 10.

FIGS. 3-7 are shown with transparent bodies for ease of illustration of the flow channels and internal elements. The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
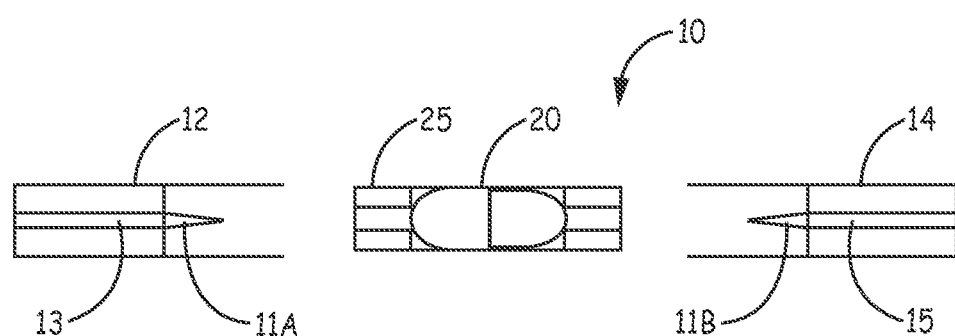

Referring now to FIG. 1 and FIG. 2, the flavoured nicotine powder inhalers 10 include a mouthpiece portion 12 and a distal end portion 14 and a nicotine capsule 20 disposed between them. Piercing elements 11A and 11B are configured to pierce the capsule 20 and fluidly connect the airflow channel 13 of the mouthpiece portion 12 with the airflow channel 15 of the distal end portion 14. The airflow channel extends linearly along a length of the nicotine powder inhaler 10. FIG. 2 further illustrates the capsule 20 within a receptacle 25 that can be re-usable. A flavour delivery element can be upstream, downstream or within the capsule 20.

Figure 3:
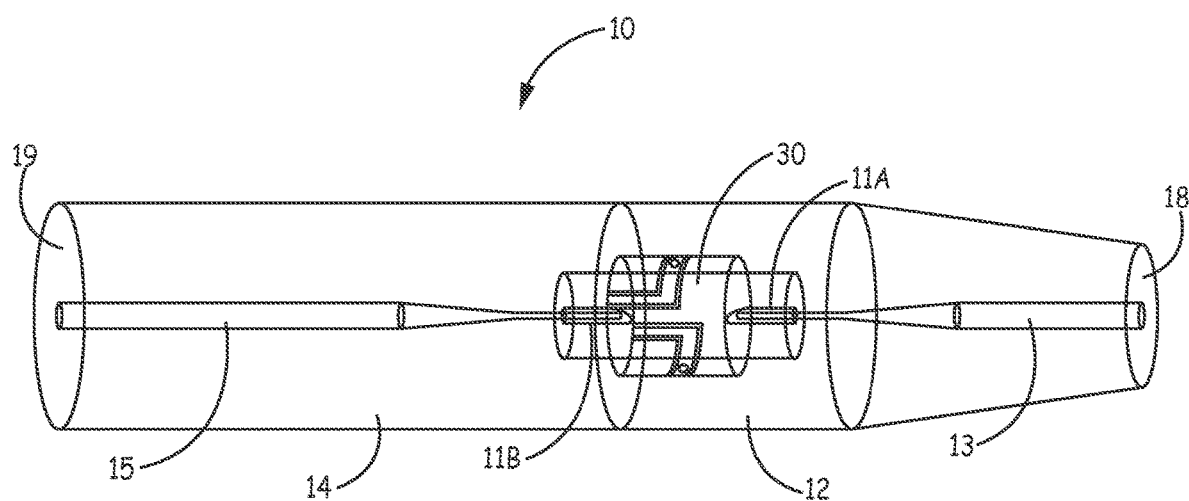
Figure 4:
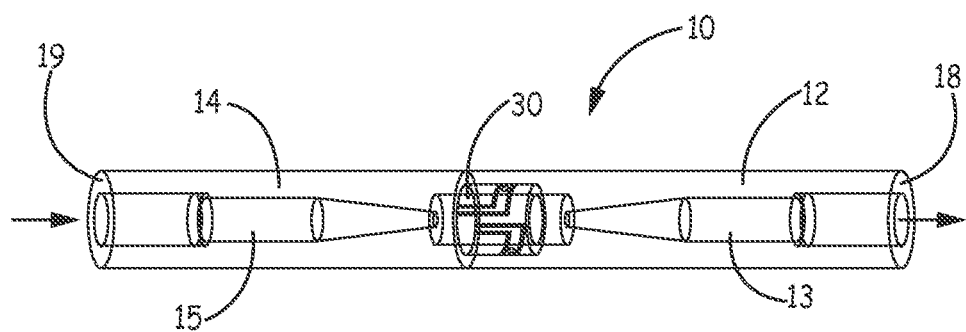

FIG. 3 and FIG. 4 illustrate flavoured nicotine powder inhalers 10 having a single linear airflow channel 13, 15. Piercing elements 11A and 11B extend into a nicotine powder receptacle 30 and are configured to pierce the nicotine powder capsule and fluidly connect the airflow channel 13 of the mouthpiece portion 12 with the airflow channel 15 of the distal end portion 14. The airflow channel extends linearly along a length of the nicotine powder inhaler 10 from a proximal mouthpiece end 18 to a distal end 19. The mouthpiece portion 12 can connect with the distal end portion 14 via a bayonet-type connection. In FIG. 3 the mouthpiece portion 12 is not symmetrical with the distal end portion 14. In FIG. 4 the mouthpiece portion 12 is symmetrical with the distal end portion 14. A flavour delivery element can be disposed along the airflow channel 13, 15 and can be pierced with the piercing elements 11A and 11B or separate set of piercing elements, not illustrated.

Figure 5:
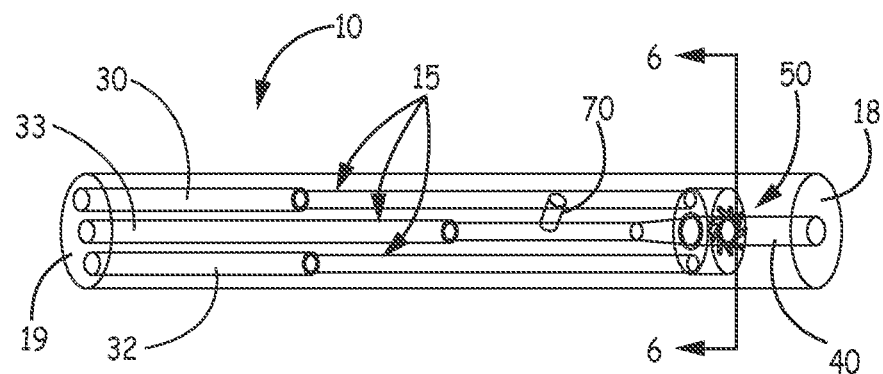
Figure 6:
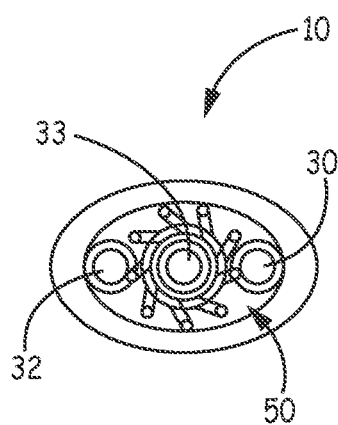

FIG. 5 and FIG. 6 is a further illustrative flavoured nicotine powder inhaler 10 having multiple airflow channels 15. FIG. 6 is a view of FIG. 5 taken along lines 6-6. This embodiment includes three airflow channels 15 and a first, second and third powder receptacles 30, 32 and 33 respectively. A nicotine powder capsule and flavour capsule can be received in at least one of the powder receptacles 30, 32 and 33. In some embodiments, a second active agent can be received in at least one of the powder receptacles 30, 32 and 33. The three flow channels 15 fluidly connect to an outlet channel 40 via a swirl generator 50 configured to induce rotation movement in the airflow. The airflow channels 15 extend linearly along a length of the flavoured nicotine powder inhaler 10 from a proximal mouthpiece end 18 to a distal end 19. A ventilation element 70 can be disposed along an airflow channels 15 to provide dilution air, as desired.

Figure 7:
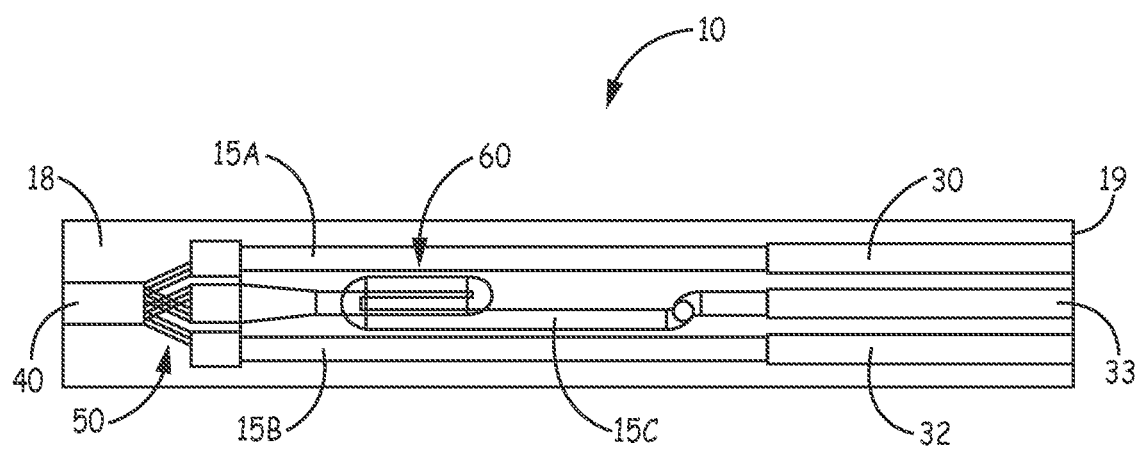

FIG. 7 is a further illustrative flavoured nicotine powder inhaler 10. This embodiment includes three airflow channels 15A, 15B and 15C and first, second and third powder receptacles 30, 32 and 33 respectively. A nicotine powder capsule and flavour capsule can be received in at least one of the powder receptacles 30, 32 and 33. In some embodiments, a second active agent can be received in at least one of the powder receptacles 30, 32 and 33. The three flow channels 15 fluidly connect to an outlet channel 40 via a swirl generator 50 configured to induce rotation movement in the airflow. The airflow channels 15A, 15B extend linearly along a length of the flavoured nicotine powder inhaler 10 from a proximal mouthpiece end 18 to a distal end 19. In some embodiments an airflow loop element 60 is disposed along an airflow channels 15C.

Figure 8:
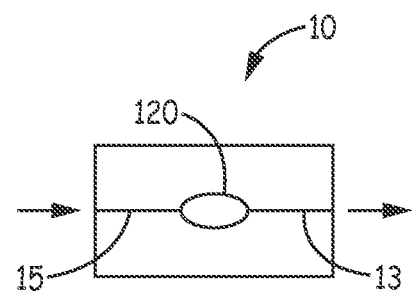

FIGS. 8-11 illustrate schematic diagrams of flavoured inhalers 10. FIG. 8 shows a flavoured nicotine inhaler 10 having a single flow path and a single capsule 120 containing both the powdered nicotine and flavourant, preferably a powdered flavourant. The air flow path includes an upstream portion 15 and a downstream portion 13.

Figure 9:
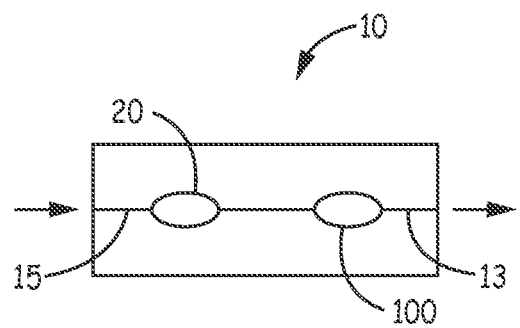

FIG. 9 shows a flavoured nicotine inhaler 10 having a single flow path and a nicotine capsule 20 containing powdered nicotine in serial flow arrangement with the flavourant capsule 100, preferably a powdered flavourant. In some embodiments the flavourant capsule 100 contains a liquid flavourant. In many of these embodiments the flavourant capsule 100 can be ruptured by a user to release the liquid flavourant, as described above. The liquid flavourant is preferably downstream of the nicotine capsule 20. The air flow path includes an upstream portion 15 and a downstream portion 13.

Figure 10:
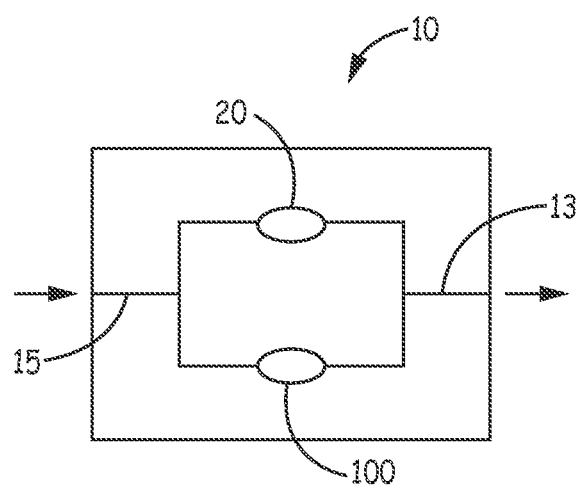

FIG. 10 shows a flavoured nicotine inhaler 10 having a parallel flow path and a nicotine capsule 20 containing powdered nicotine in parallel flow arrangement with the flavourant capsule 100, preferably a powdered flavourant. In some embodiments the flavourant capsule 100 contains a liquid flavourant. The flavourant capsule 100 can be pierced as described above for the nicotine capsule 20. The air flow path includes an upstream portion 15 and a downstream portion 13.

Figure 11:
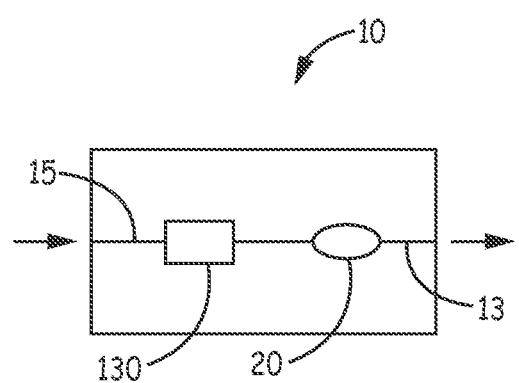

FIG. 11 shows a flavoured nicotine inhaler 10 having a single flow path and a nicotine capsule 20 containing powdered nicotine in serial flow arrangement with the flavour delivery element 130. The flavour delivery element 130 can be a filter element having a thread impregnated with flavourant, preferably liquid flavourant. The nicotine capsule 20 is preferably downstream of the filter element providing the flavourant. The air flow path includes an upstream portion 15 and a downstream portion 13.

The invention claimed is:

1. A nicotine powder inhaler comprising:
    a body extending between a mouthpiece portion and a distal end portion;
    a nicotine powder receptacle disposed within the body;
    a filter element disposed in the airflow channel, comprising a plug of filter material;
    a swirl generator element constructed to induce rotational movement in the airflow moving through the body;
    a plurality of inlet airflow channels extending from the distal end portion to the swirl generator; and
    an outlet airflow channel extending axially from the swirl generator and the nicotine powder receptacle to an outlet at a proximal end of the mouthpiece portion,
    wherein the inhaler is constructed to deliver a dose of nicotine powder into lungs of a user via air flow created by inhalation at the mouthpiece portion at an inhalation rate of less than about 5 L/min.

2. The nicotine powder inhaler of claim 1, wherein the filter element is formed of filtration material comprising cellulose acetate wrapped in paper or plug wrap.

3. The nicotine powder inhaler of claim 1 further comprising a dose of flavourant disposed within the filter element.

4. A system for providing nicotine powder, the system comprising the nicotine powder inhaler of claim 1 and further comprising a capsule containing a dose of nicotine powder and a dose of flavourant, the capsule disposed inside the nicotine powder receptacle.

5. A nicotine powder inhaler according to claim 1, further comprising a piercing element configured to pierce a capsule of nicotine powder received in the nicotine powder receptacle.

6. The system of claim 4, wherein the dose of flavourant comprises powdered flavourant.

7. The system of claim 4, wherein the dose of flavourant comprises liquid flavourant.

8. The system of claim 4, wherein the dose of flavourant is contained in a crushable capsule that can be ruptured by a user to release flavourant.

9. The system of claim 4, wherein the filter element is disposed upstream of the nicotine powder receptacle.

10. The system of claim 9, wherein the filter element comprises a thread impregnated with menthol.

11. The system of claim 4, further comprising a dose of active agent.

12. The system of claim 4, wherein the nicotine powder has a mean average diameter size in a range from 1 to 7 micrometers.

13. The system of claim 12, wherein at least 90% of the nicotine powder has a particle size of 10 micrometers or less.

14. The system of claim 4, wherein the nicotine powder comprises L-leucine.

15. The system of claim 14, wherein the nicotine powder comprises nicotine bitartrate.

16. The system of claim 4, wherein the dose of flavourant comprises one of more flavors selected from tobacco, smoke, menthol, mint, chocolate, licorice, citrus, fruit flavour, gamma octalactone, vanillin, ethyl vanillin, a breath freshener flavour, cinnamon, methyl salicylate, linalool, bergamot oil, geranium oil, lemon oil, ginger oil, phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, and combinations thereof.

17. The system of claim 4, wherein the dose of nicotine comprises an amount of nicotine powder sufficient to deliver from 5 to 50 puffs of nicotine, each puff comprising from 0.5 mg to 3 mg of nicotine.

18. A method of inhaling flavoured nicotine into lungs of a user, the method comprising:
    inhaling air through the flavoured nicotine power inhaler according to claim 1 at a flow rate of less than about 2 L/min to deliver flavoured powder nicotine into lungs of a user.

19. A method according to claim 18, wherein the inhaling air through the nicotine power inhaler induce rotational movement of air flowing through the nicotine powder inhaler.

20. The method of claim 18, wherein delivering flavoured powder nicotine comprises delivering a portion of a dose of nicotine powder contained in the nicotine powder receptacle.

21. The method of claim 18, wherein delivering flavoured powder nicotine comprises a puff, and wherein a dose of nicotine powder contained in the nicotine powder receptacle comprises an amount of nicotine powder sufficient to deliver from 5 to 50 puffs.

* * * * *